(12) United States Patent
Mazor et al.

(10) Patent No.: US 6,184,686 B1
(45) Date of Patent: Feb. 6, 2001

(54) CONTAMINATION AND RESIDUALS INSPECTION SYSTEM

(75) Inventors: Isaac Mazor, Haifa; Amos Gvirtzman, Zippori; Reuven Duer, Karkur, all of (IS)

(73) Assignee: Jordan Valley Applied Radiation Ltd., Migdal Ha'emek (IS)

( * ) Notice: Under 35 U.S.C. 154(b), the term of this patent shall be extended for 0 days.

(21) Appl. No.: 09/114,462

(22) Filed: Jul. 13, 1998

(51) Int. Cl.$^7$ ................................................. G01N 27/62
(52) U.S. Cl. ........................ 324/464; 324/751; 324/537
(58) Field of Search ........................... 250/214.1, 305, 250/306, 206, 372, 288, 282; 378/44, 45, 49; 324/464, 459, 501, 522, 523, 531, 537, 750, 751

(56) References Cited

U.S. PATENT DOCUMENTS

| | | | |
|---|---|---|---|
| 5,138,158 | * 8/1992 | Ninomiya et al. | 250/305 |
| 5,508,627 | * 4/1996 | Patterson | 324/752 |
| 5,584,938 | * 12/1996 | Douglas | 134/1.3 |
| 5,742,658 | * 4/1998 | Tiffin et al. | 378/44 |

OTHER PUBLICATIONS

K. Siomos, "Laser Multiphoton Ionization Spectroscopy of Polyatomic Molecules," *Technical University of Crete, Greece*, pp. 263–325.

V. V. Gridin et al., "Particulate Material Analysis by a Laser Ionization Fast Conductivity Method. Water Content Effects," *Analytical Chemistry*, vol. 69, pp. 478–484 (1997).

V. V. Gridin et al., "Laser Two–Photon Ionization of Pyrene on Contaminated Soils," *Analytical Chemistry*, vol. 68, pp. 3359–3363 (1996).

T. Inoue et al., "Highly Sensitive Detection of Aromatic Molecules by Laser Two–Photon Ionization on the Surface of Water in Ambient Air," *Analytical Chemistry*, vol. 66, pp. 1012–1014 (1994).

S. Yamada et al., "Trace Determination of Some Aromatic Molecules by Laser Two–Photon Ionization," *Analytica Chimica Acta*, vol. 183, pp. 251–256 (1986).

* cited by examiner

*Primary Examiner*—Andrew Tran
*Assistant Examiner*—Bradley K Smith
(74) *Attorney, Agent, or Firm*—Lahive & Cockfield, LLP

(57) ABSTRACT

A method and apparatus for detecting a contaminant in a substrate. An array of anode elements is positioned in proximity to the substrate and is biased at a positive voltage relative to the substrate. The substrate is irradiated with photons having energies below an atomic ionization energy of the substrate, so as to ionize the contaminant to emit electrons. The emitted electrons are collected at one or more of the anode elements, thereby generating a current indicative of the presence of the contaminant in the semiconductor in proximity to the one or more of the anode elements.

8 Claims, 6 Drawing Sheets

CONTAMINATION AND RESIDUALS INSPECTION SYSTEM

FIELD OF THE INVENTION

The present invention relates generally to detection of trace materials in manufacturing processes, and specifically to contamination detection in semiconductor manufacturing.

BACKGROUND OF THE INVENTION

Contamination and residuals (C&R) detection is an integral part of the manufacture of semiconductor components. Typical contaminants found in the manufacturing process are impurities present in the liquid used to dissolve photoresist layers. A typical residual is a portion of photoresist, which is commonly polymethylmethacrylate (PMMA). As the size of the components decreases and their complexity grows, the effect of a specific contaminant on the component becomes more acute, and the detection of contaminants and also of residual chemicals becomes more important. In *Rapid Thermal Processing,* edited by Richard Fair, Academic Press, Inc., which is incorporated herein by reference, the author gives an example of a "killer" defect size in semiconductor processing for a gate thickness of 7 nm, wherein a defect sized 3.5 nm could be fatal. Typically, a rule of thumb for a killer defect size is that the defect is of the order of half the size of the design rule used.

Although both wet and dry cleaning processes are used in the manufacture of semiconductor components, neither is completely effective in removing contaminants, such as residues of photoresist, from the surface of the wafer. Typically this is compensated for by cleaning the wafer by about 30% more than the optimal cleaning time, entailing extra cost, time and increased possibility of damaging the components on the wafer.

There are many processes known in the art for C&R detection. In high-speed optical defect review systems, which are typically integrated into a production line for components, the cost of inspection is relatively high. In addition, for some layers such systems only allow low sampling rates, and do not detect non-visible residuals for any layers.

An alternative system for C&R detection is optical spectral analysis, wherein photons from pre-ionized contaminants are detected, usually by a CCD array detector. However, in order to evaluate if the photons are from a contaminant, the optical spectral analysis system has to analyze the wavelength of the received photons.

While any C&R detection process is operating, it must be absolutely non-destructive to components being checked.

SUMMARY OF THE INVENTION

It is an object of some aspects of the present invention to provide an improved method and apparatus for the detection of contaminants and residuals, particularly in semiconductor manufacture.

In some preferred embodiments of the present invention, a plurality of anodes is scanned across a surface, typically the surface of a semiconducting wafer, with the wafer preferably acting as a cathode. Simultaneously, the area of the wafer in the region of the anodes is irradiated with a high flux of low energy photons, preferably in the optical or near-ultraviolet (UV). The wavelength of the radiation is chosen so that the photon energy is substantially below the ionization level of substrate atoms in the wafer, so that substantially no photoelectrons are generated therefrom, and so that no defects are introduced into the wafer. Contaminants and residuals on the surface of the wafer are ionized by a process of photon absorption, most preferably by a process of two-photon absorption (TPA), and the electrons produced by the ionization are collected by the individual anodes, generating a displacement and/or an electronic current, herein referred to collectively as a current, therefrom. The current at an anode gives a measure of the size of the contaminant or residual at the position of the anode.

In some preferred embodiments of the present invention, the anodes are arranged as a substantially linear array.

In some preferred embodiments of the present invention, the signal created by a residual photoresist on the wafer is enabled or substantially enhanced by using doped photoresist.

In some preferred embodiments of the present invention, the distance of the plurality of anodes is maintained at a substantially fixed distance from the wafer by means of a high speed servo loop.

In some preferred embodiments of the present invention, a plurality of cathodes is provided in registration with the plurality of anodes, so that the cathodes enhance and/or control the field at the surface of the wafer.

In some preferred embodiments of the present invention, the anodes are fixedly positioned above selected areas of the wafer, rather than scanned over the surface, as described hereinabove.

There is therefore provided, in accordance with a preferred embodiment of the present invention, a method of detecting a contaminant in a substrate, including:

positioning an array of anode elements in proximity to the substrate;

biasing the array at a positive voltage relative to the substrate;

irradiating the substrate with photons having energies below an atomic ionization energy of the substrate, so as to ionize the contaminant to emit electrons; and collecting the emitted electrons at one or more of the anode elements, thereby generating a current indicative of the presence of the contaminant in the semiconductor in proximity to the one or more of the anode elements.

Preferably, irradiating the substrate includes ionizing the contaminant by a process of two-photon absorption.

Alternatively, irradiating the substrate includes irradiating over a generally linear area parallel to an axis of the array.

Preferably, irradiating over the generally linear area includes irradiating through a plurality of irradiation segments arranged over the area.

Preferably, irradiating through the plurality of irradiation segments includes irradiating through a plurality of segments simultaneously.

Alternatively, irradiating through the plurality of irradiation segments includes scanning an irradiation beam over a plurality of segments sequentially.

Preferably, collecting the emitted electrons includes determining a location of the contaminant responsive to the current from the one or more of the anode elements.

Preferably, collecting the emitted electrons includes sampling the plurality of anodes simultaneously.

Preferably, collecting the emitted electrons includes sampling the plurality of anodes sequentially.

Preferably, positioning the array includes arranging a plurality of anode elements in a linear array.

In a preferred embodiment, the method includes positioning an array of cathode elements in proximity to the substrate and to the array of anodes and biasing the cathode elements at a negative voltage relative to the substrate.

Preferably, biasing the cathode elements includes setting the cathode voltage so as to enhance the current indicative of the presence of the contaminant.

Alternatively or additionally, biasing the cathode elements includes setting the cathode voltage so as to discriminate between currents created by different types of contaminant.

Preferably, positioning the array includes scanning the array over an area of the substrate that is irradiated.

Preferably, scanning includes scanning the array in a generally linear pattern relative to the substrate.

Alternatively, scanning includes rotating the substrate, so that the array is scanned in a generally circular pattern relative thereto.

Preferably, positioning the array includes maintaining a constant distance between the semiconductor and the anode, preferably by measuring an electric field between the semiconductor and the anode, and adjusting the distance therebetween in response thereto.

Preferably, the substrate includes a semiconductor wafer, and the method includes applying to the semiconductor wafer a photoresist including a dopant having a high absorption cross-section for the irradiating photons.

Preferably, the dopant has a high two-photon absorption cross-section.

There is further provided, in accordance with a preferred embodiment of the present invention, apparatus for detecting a contaminant in a substrate, including:

an irradiator which irradiates the substrate with photons having energies below an atomic ionization energy of the substrate, so as to ionize the contaminant to produce electrons; and an array of anode elements, which is positioned adjacent to the substrate and biased at a positive voltage with respect thereto, so as to collect the electrons, thereby generating a current indicative of the presence of the contaminant in the semiconductor.

Preferably, the photons ionize the contaminant by a process of two-photon absorption.

Preferably, the irradiator irradiates the substrate over a generally linear region thereof.

Preferably, the array includes a plurality of anodes in a generally linear arrangement.

Alternatively or additionally, the apparatus includes a positioning device for maintaining a constant distance between the semiconductor and the anode.

Preferably, the apparatus includes a scanner, which scans the array over a surface of the substrate.

In a preferred embodiment, the apparatus includes an array of cathode elements positioned in proximity to the substrate and to the array of anodes and biased at a negative voltage relative to the substrate.

Preferably, the cathode elements are biased so as to enhance the current indicative of the presence of the contaminant.

Alternatively or additionally, the cathode elements are biased so as to discriminate between currents created by different types of contaminant.

There is further provided, in accordance with a preferred embodiment of the present invention, photoionization detector apparatus, including:

a generally transparent plate, which is brought into proximity with a material to be photoionized and through which a beam of radiation impinges on the material; and an array of electrodes, formed on a surface of the plate adjacent to the material and electrically biased relative to the material, so as to collect charged particles emitted from the material responsive to the beam of radiation.

Preferably, the array of electrodes includes a plurality of electrodes in a generally linear arrangement.

Preferably, the plurality of electrodes includes a first and a second linear array of electrodes separated by a generally linear aperture.

In a preferred embodiment, the first linear array includes an anode array, and the second linear array includes a cathode array.

In another preferred embodiment, the array of electrodes includes a plurality of electrodes arranged in a two-dimensional matrix.

Preferably, the generally linear aperture transmits the beam of radiation.

Preferably, the apparatus includes a positioning device for maintaining a generally constant distance between the material and the array.

Preferably, the positioning device includes an array scanner, which scans the array over the material.

Alternatively or additionally, the apparatus includes a beam scanner which scans the beam of radiation over the material.

The present invention will be more fully understood from the following detailed description of the preferred embodiments thereof, taken together with the drawings in which:

DETAILED DESCRIPTION OF PREFERRED EMBODIMENTS

Figure 1:
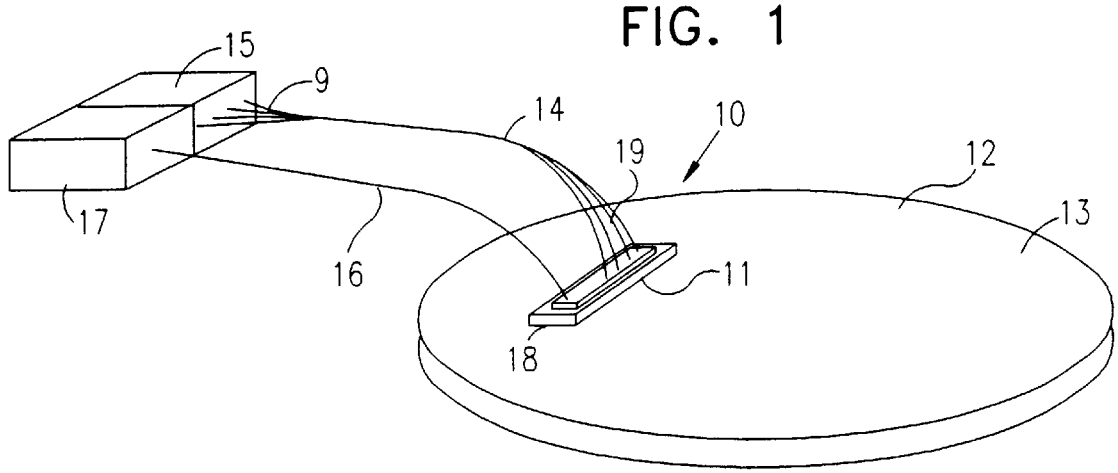
FIG. 1 is a schematic perspective view showing operation of a contaminant detector, in accordance with a preferred embodiment of the present invention.

Reference is now made to FIG. 1, which shows a perspective view of a contaminant and residual detector 10, in accordance with a preferred embodiment of the present invention. Detector 10 comprises a substantially planar lower surface 11, which is positioned close to, but not touching, a wafer 12 having an upper surface 13 which is to be checked for contaminants or residues. Preferably wafer 12 is a semiconducting wafer. Preferably detector 10 is positioned by a positioning unit (not shown), of any suitable type known in the art, so that lower surface 11 is of the order of 10 $\mu$m from upper surface 13 of wafer 12.

Detector 10 comprises a fiberoptic cable 14, which is attached to detector 10 so as to allow light from the fiberoptic cable to irradiate wafer 12 at an angle substantially perpendicular to the wafer. Preferably lower surface 11 is formed from sapphire, to enable the irradiating light to penetrate to the wafer. Alternatively lower surface 11 is formed from quartz. The method of irradiation is described in more detail hereinbelow.

A light and processing unit 17 comprises a light source 15 coupled to fiberoptic 14. Preferably, fiberoptic cable 14 is coherent, with a first linear termination 9 and a corresponding second linear termination 19. Preferably, the light entering fiberoptic 14 comprises a high flux of low energy photons, typically having energies of the order of 5 eV. Most preferably, the wavelength of the light is such that the photon energy is substantially less than the ionization energy level of substrate atoms of wafer 12 (so that substantially no defects are introduced and no ionization occurs during irradiation thereof) but of sufficient energy that photon absorption by contaminant or residual molecules may occur, causing the molecules to ionize.

In a preferred embodiment, light source 15 comprises an ultraviolet laser source, such as an excimer laser or a frequency-multiplied solid-state laser, as are known in the art. Alternatively, the light source comprises a tunable laser, such as a frequency-multiplied dye laser, which is tuned for determination of specific residuals. The photon energy is chosen and/or adjusted so that ionization of contaminant or residual molecules occurs by a process of two-photon absorption, substantially without ionization of the substrate. For example, in the case of contaminant or residual molecules having ionization energies of 10 eV or less, photon energies of 5 eV may be used. Optionally, fiberoptic 14 is replaced by suitable beam scanning and focusing optics, including a polygon or galvanometrically-scanned mirror, for example, so that the laser beam is incident on wafer 12 with sufficient energy flux to give a high two-photon ionization signal, as described further hereinbelow.

Figure 2A:
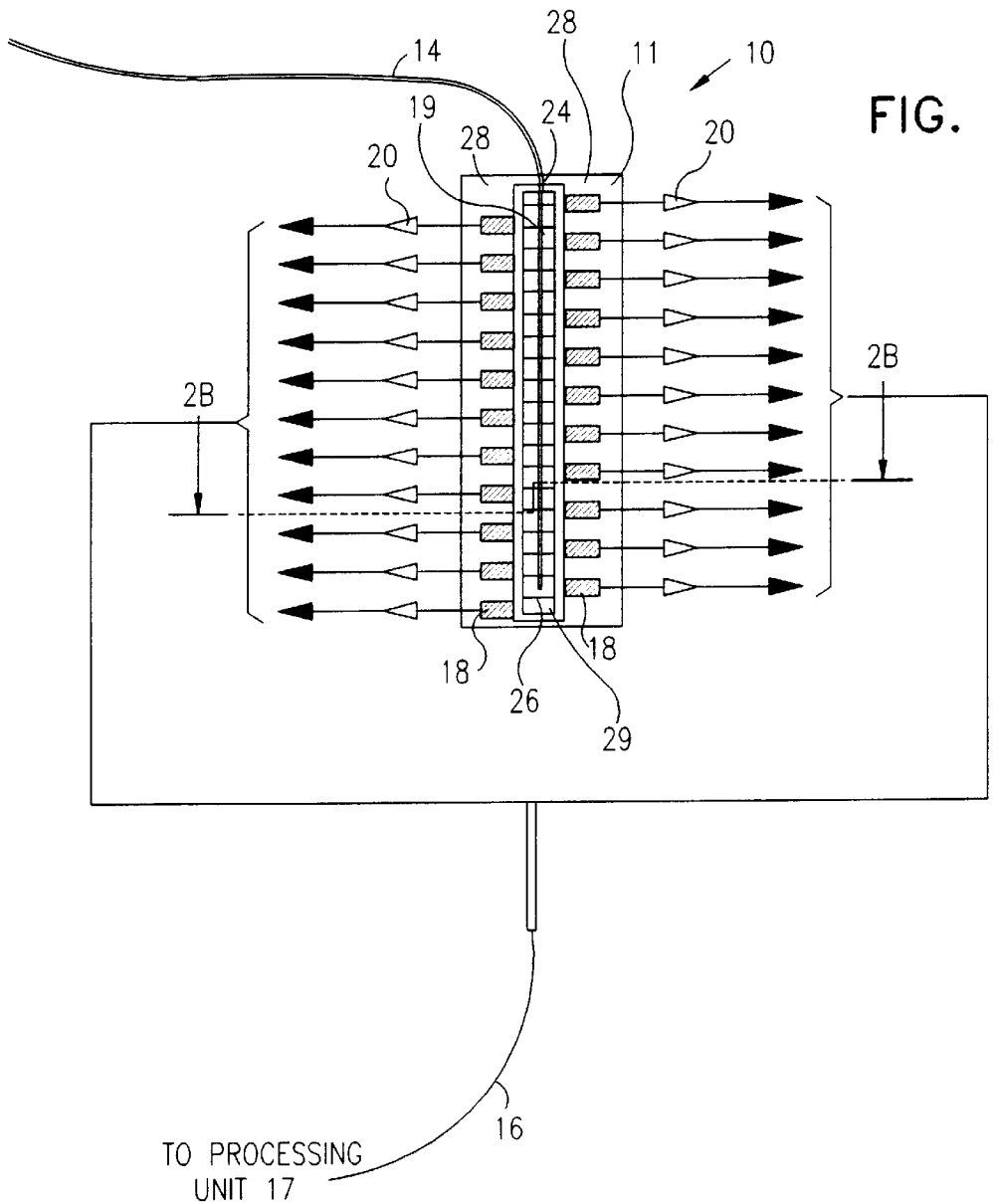
FIG. 2A is a schematic view of the lower surface of a contaminant detector viewed from below, in accordance with a preferred embodiment of the present invention.
Figure 2B:
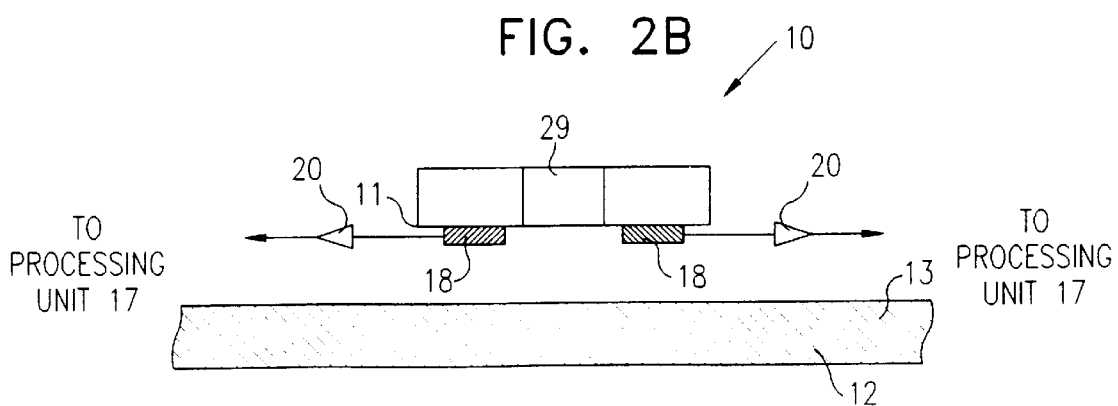
FIG. 2B is a schematic cross-section along a line 2B—2B of FIG. 2A.

FIG. 2A shows a schematic view of lower surface 11 of detector 10 viewed from below, in accordance with a preferred embodiment of the present invention. FIG. 2B shows a schematic cross-sectional view of detector 10, taken along line 2B—2B of FIG. 2A. Lower surface 11 comprises a plurality of anodes 18, which are connected by a cable 16 to processing unit 17. Preferably, anodes 18 are formed on lower surface 11 by first etching then depositing on the etched area metallic, most preferably chrome, pads. During operation, ionized electrons from contaminant or residual molecules are collected by at least one of the plurality of anodes, and a corresponding signal is transmitted to unit 17. Wafer 12 is electrically grounded or biased to act as a cathode, thereby completing the circuit and ensuring there is no charge build up on wafer 12. Unit 17 processes the incoming signals, and generates an output showing the position of contaminants or residuals on surface 13 by identifying from which of anodes 18 the signal originated.

Anodes 18 are preferably arranged in a pair of lines 28 having a slot 24 between the lines. Preferably, anodes 18 are substantially square having dimensions of the order of 20 $\mu$m by 20 $\mu$m, respectively separated by 20 $\mu$m, and slot 24 is of the order of 20 $\mu$m wide. Anodes 18 are respectively connected to a plurality of low noise preamplifiers 20, which transmit amplified signals to cable 16. While preamplifiers 20 are shown as separate from their corresponding anodes in FIG. 2A and FIG. 2B, it will be appreciated that the plurality of anodes and corresponding preamplifiers may be constructed as an integrated unit, by methods known in the art, on surface 11. Preferably, during operation of detector 10, anodes 18 are sampled sequentially, and signals therefrom are transmitted to unit 17. Alternatively, anodes 18 are sampled simultaneously.

An irradiator 26, comprising a plurality of irradiation segments 29 corresponding respectively to anodes 18, is coupled to termination 19 of fiberoptic 14 and is positioned over slot 24. Irradiator 26 is constructed so as to accept light from fiberoptic 14 and direct the light downwards through segments 29 to surface 13 of wafer 12 of FIG. 1. Preferably, light from fiberoptic 14 is sequentially transmitted to the plurality of irradiation segments, by light source 15 sequentially scanning across termination 9 of fiberoptic 14, causing simultaneous scanning across termination 19. Alternatively, light from fiberoptic 14 is simultaneously transmitted to the plurality of irradiation segments. Preferably, in the case when anodes 18 are sampled sequentially and light from fiberoptic 14 is sequentially transmitted to the plurality of irradiation segments, the two operations are synchronized. Most preferably, light from fiberoptic 14 comprises photons of energy of the order of 5 eV, as described hereinabove.

Figure 3:
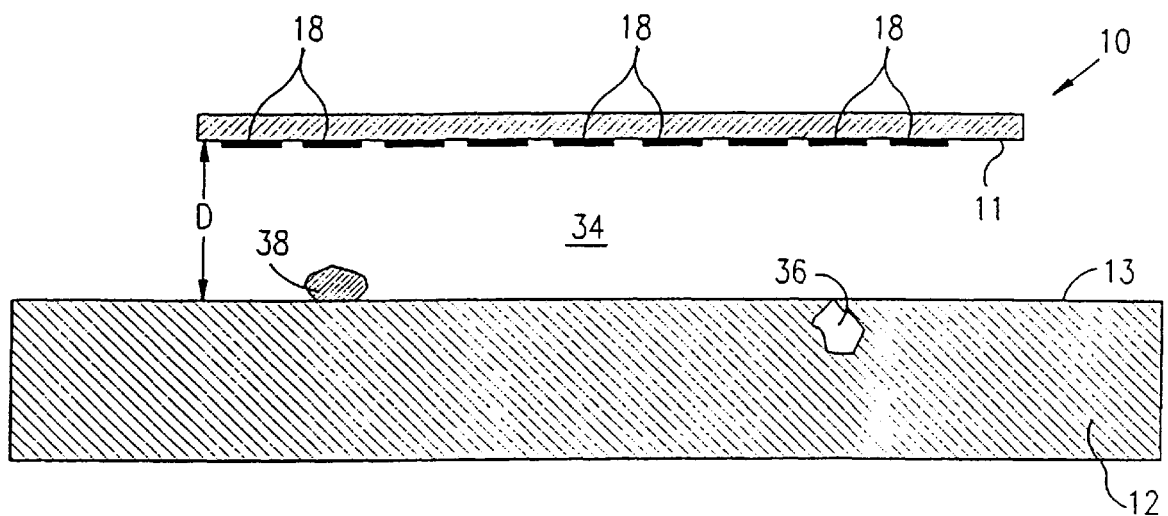
FIG. 3 is a schematic sectional side view of a contaminant detector, in accordance with a preferred embodiment of the present invention.

FIG. 3 is a schematic cross-sectional side view of detector 10 above wafer 12, in accordance with a preferred embodiment of the present invention. An air gap 34 exists between detector 10 and wafer 12. A contaminant 38, on surface 13, and a contaminant 36, below surface 13, are shown by way of example. Detector 10 is positioned so that surface 11 is substantially parallel to surface 13, and is at a distance D of the order of 10 $\mu$m therefrom. Preferably, detector 10 is supported above wafer 12 by positioning apparatus (not shown) capable of scanning detector 10 across wafer 12, and also capable of relatively speedily moving detector 10 vertically with respect to wafer 12.

Preferably, anodes 18 are electrically biased at a voltage that generates an electric field of the order of 1500 V/cm in gap 34 between the anodes and the wafer surface. Optionally, the electric field is adjusted so as to enable discrimination between photoelectrons generated by different contaminants. The electric field between the plurality of anodes and wafer 12 is measured continuously, and the vertical distance D between surfaces 11 and 13 is controlled using a high speed closed servo loop so as to maintain the electric field in air gap 34 substantially constant, thereby maintaining distance D substantially constant. Alternatively, distance D is measured optically or by other methods known in the art, and changes in the distance are corrected for as described above.

When contaminant 38 is irradiated, some of its molecules ionize producing electrons which enter air gap 34 and which are then captured by anodes 18 at the left of detector 10 to generate a current. Similarly, when contaminant 36 is irradiated, some of its molecules ionize producing electrons which are captured by anodes 18 at the right of detector 10. It will be appreciated that the value of the current generated at the respective anodes substantially depends on the size of contaminant at surface 13, and that the position of the contaminant is substantially equivalent to the position of the current generating anodes.

In some preferred embodiments of the present invention, a dopant at a concentration of the order of 1% is incorporated in the photoresist, and the doped photoresist is used during manufacture of wafer 12. Preferably, the dopant used has a high absorption cross-section for the irradiating photons. Most preferably the dopant is a nonlinear optical dye such as Rhodamine B having a high TPA cross-section, so that signals due to two-photon absorption by residual photoresist are substantially enhanced compared to using undoped photoresist.

Figure 4A:
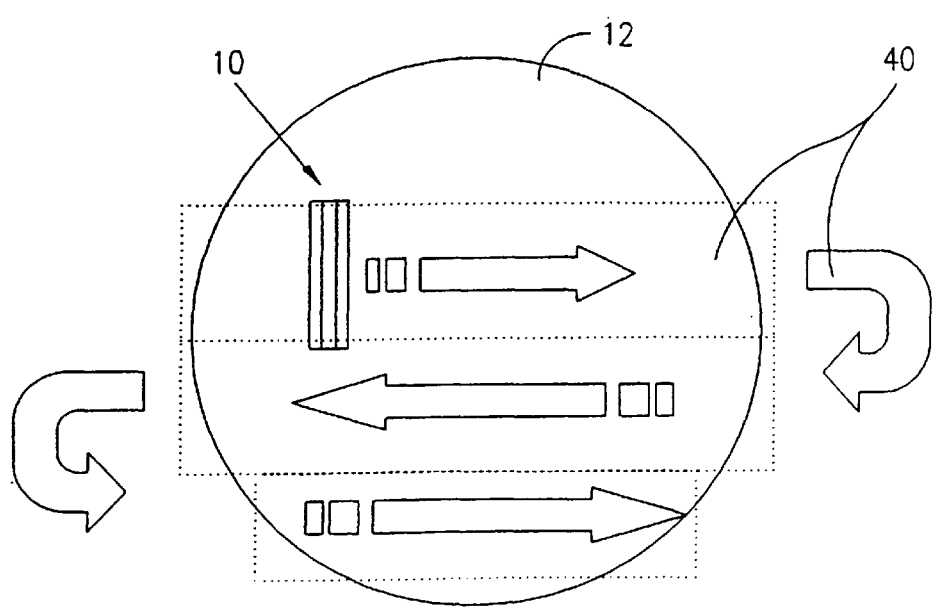
FIG. 4A is a schematic diagram showing a scanning path of a contaminant detector across a wafer, in accordance with a preferred embodiment of the present invention.

FIG. 4A is a schematic view illustrating a method of scanning wafer 12, in accordance with a preferred embodiment of the present invention. Preferably, detector 10 is scanned in a zigzag path 40 according to commands from processing unit 17 of FIG. 1, in order to scan the complete surface of wafer 12. Other scan paths, such as a raster or circular scan, are also possible. Alternatively, detector 10 is not scanned over the complete surface of wafer 12, but is moved only to one or more predefined target positions of wafer 12.

Figure 4B:
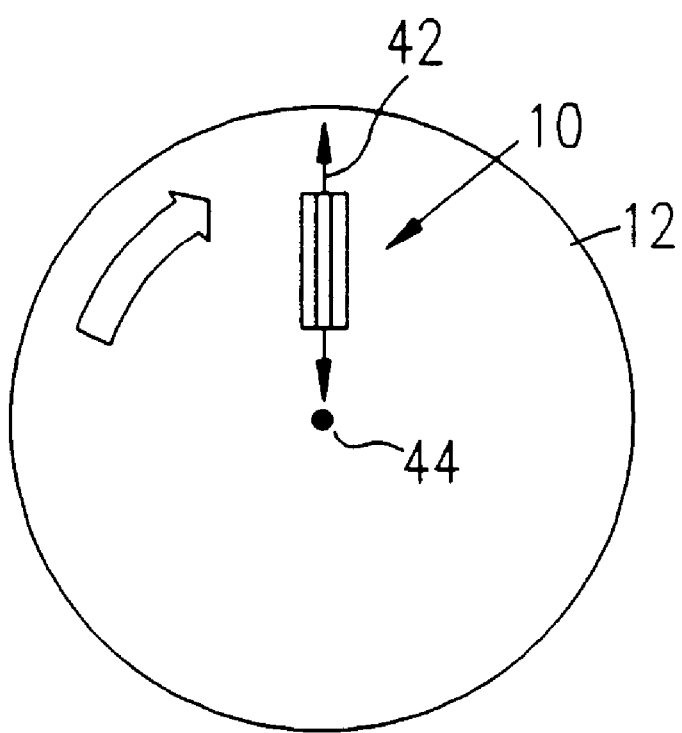
FIG. 4B is a schematic diagram showing a scanning path of a contaminant detector across a wafer, in accordance with an alternative preferred embodiment of the present invention.

FIG. 4B is a schematic view illustrating an alternative method of scanning wafer 12, in accordance with a preferred embodiment of the present invention. Preferably wafer 12 is rotated about a central axis of symmetry 44, while at the same time detector 10 is scanned in a substantially linear path 42, according to commands from processing unit 17, shown in FIG. 1.

Figure 5A:
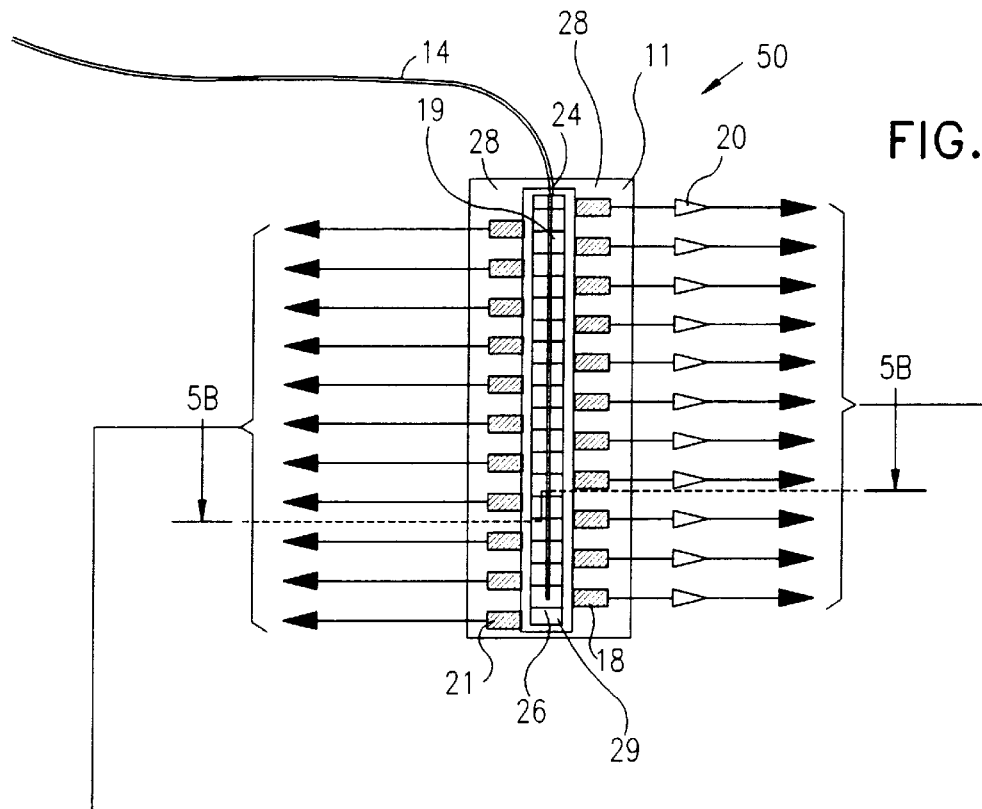
FIG. 5A is a schematic view of the lower surface of a contaminant detector viewed from below, in accordance with an alternative preferred embodiment of the present invention.
Figure 5B:
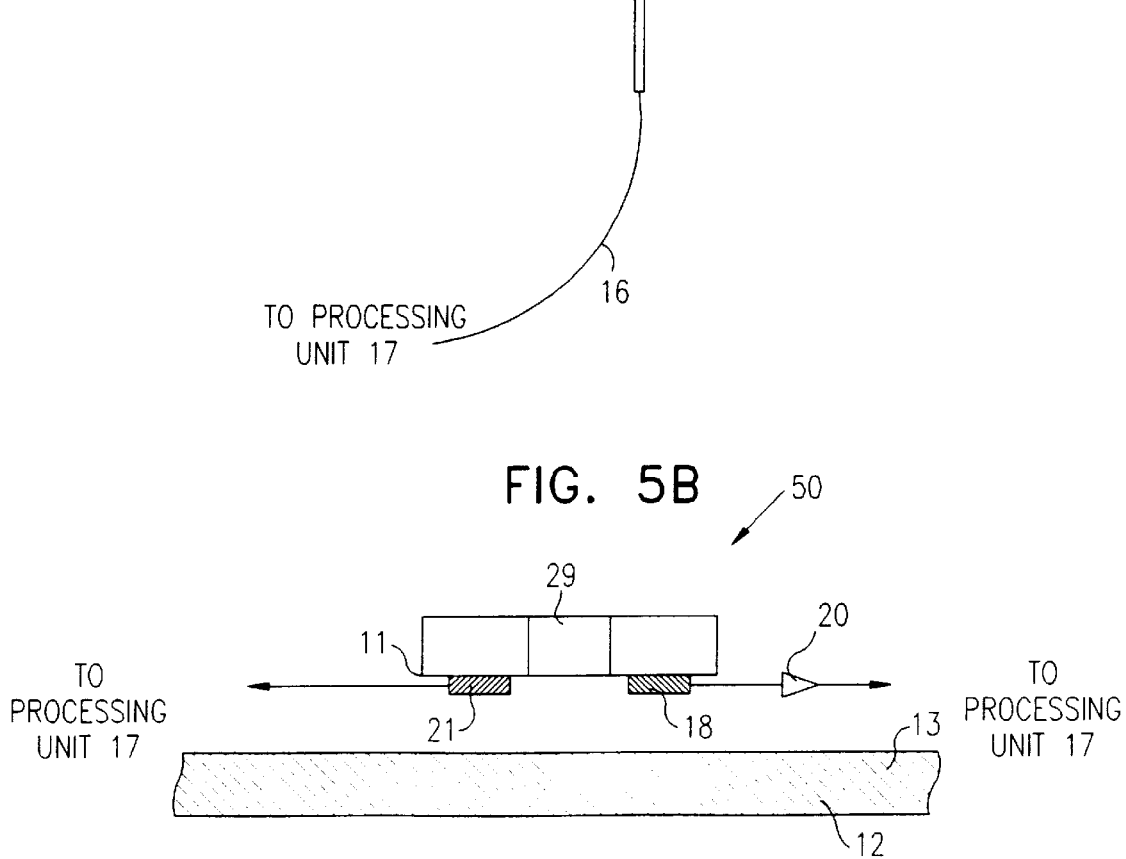
FIG. 5B is a schematic cross-section along a line 5B—5B of FIG. 5A.

Reference is now made to FIG. 5A, which shows a schematic view of a detector 50 viewed from below, in accordance with a preferred embodiment of the present invention. FIG. 5B is a schematic, cross-sectional view of detector 50, taken along line 5B—5B of FIG. 5A. Apart from the differences described below, the operation of detector 50 is generally similar to that of detector 10 (FIGS. 1–4B), whereby elements indicated by the same reference numerals in both detectors 50 and 10 are generally identical in construction and in operation.

Detector 50 comprises an array of anodes 18, operating as described above for detector 10. Detector 50 also comprises a plurality of cathodes 21, most preferably arranged as a linear array parallel to the array of anodes. Cathodes 21 most preferably have substantially similar dimensions as those of anodes 18. Cathodes 21 are coupled to processing unit 17, which controls a potential applied to the cathodes. During operation of detector 50, unit 17 adjusts the potential of cathodes 21 so that the cathodes alter the field between anodes 18 and wafer 12, thereby acting as control electrodes for electrons produced in wafer 12 and collected by anodes 18. It will be appreciated that adjustment of the potential of cathodes 21 can enhance the current created at anodes 18 and can also enable anodes 18 to discriminate between current created by different contaminants.

Figure 6A:
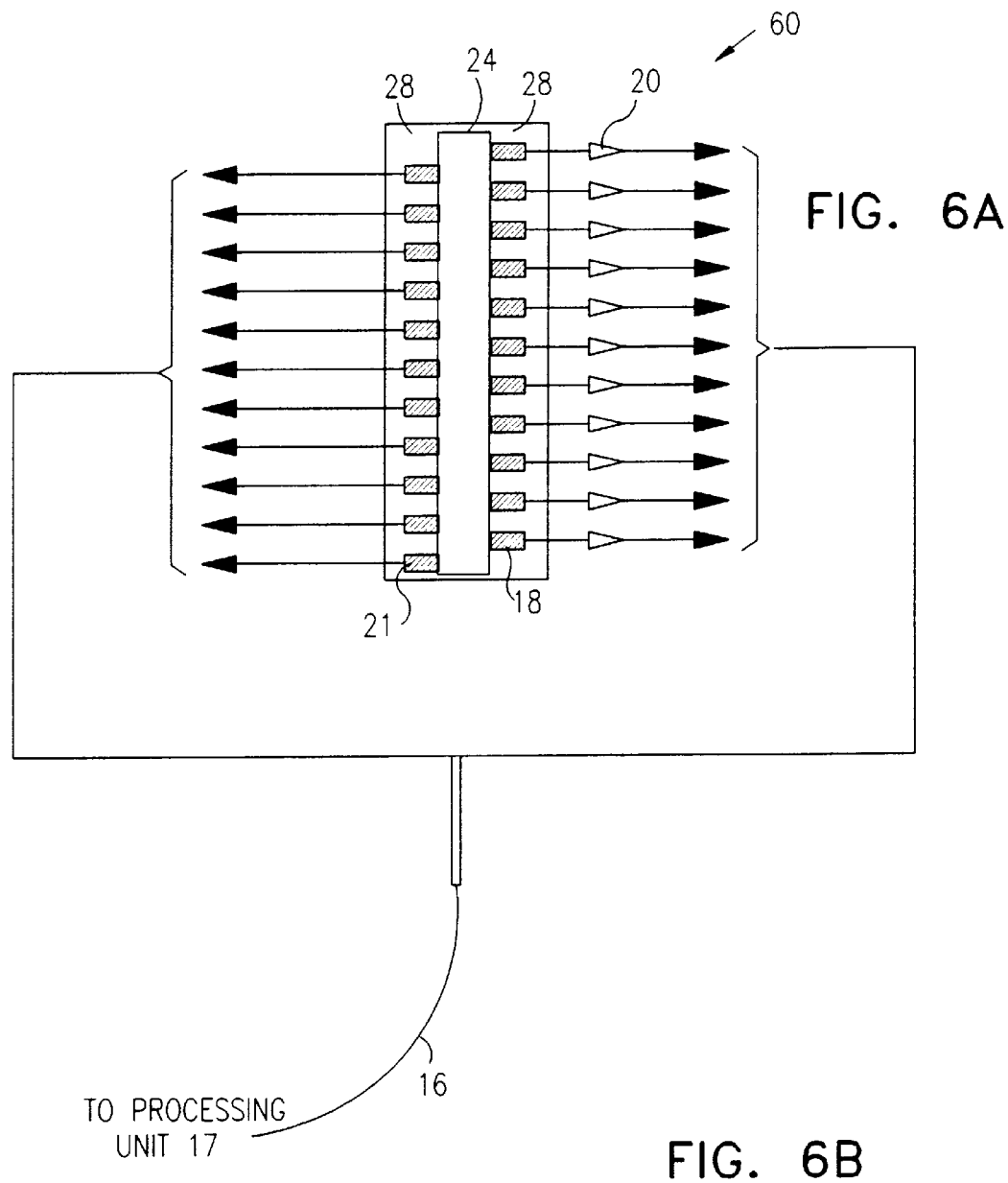
FIG. 6A is a schematic view of the lower surface of a contaminant detector viewed from below, in accordance with still another preferred embodiment of the present invention.

FIG. 6A shows a schematic view of a detector 60 viewed from below, in accordance with a preferred embodiment of the present invention. Apart from the differences described hereinbelow, the operation of detector 60 is generally similar to that of detector 10 (FIGS. 1–4B), whereby elements indicated by the same reference numerals in both detectors 60 and 10 are generally identical in construction and in operation. Detector 60 is designed to be mounted and held still over a selected area of a surface being inspected, and also does not necessarily include a termination for fiberoptic cable 14.

Figure 6B:
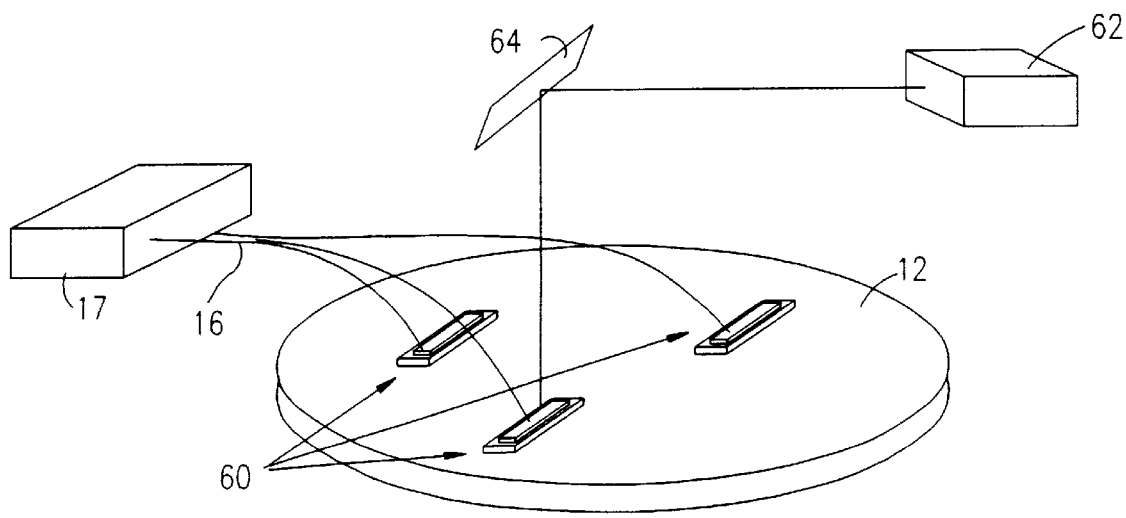
FIG. 6B is a schematic perspective view showing operation of contaminant detectors of FIG. 6A, in accordance with a preferred embodiment of the present invention.

FIG. 6B is a schematic view of a static array of detectors 60, in accordance with a preferred embodiment of the present invention. One or more detectors 60 are fixedly placed at predetermined positions above wafer 12, most preferably at positions where the likelihood of contaminants is known to be large, such as near corners of vias or, alternatively or additionally, at positions where contaminant presence is critical, such as semiconductor gates. Although detectors 60 are shown in FIG. 6B above only small, selected areas of wafer 12, a more extensive two-dimensional matrix of detectors could be used to cover a substantial area of the wafer surface or even the entire surface. In this case, the detectors are preferably coupled to a suitable shift register for addressing each of anodes 18 in turn. Furthermore, it will be understood that other detectors described hereinabove, such as detector 10, may be used in the static detection mode of FIG. 6B, and that likewise, detector 60 may be scanned over the wafer surface.

Preferably, light from a light source 62, most preferably a laser, is scanned by a movable and/or rotatable mirror 64, so that the beam from the source strikes wafer 12 at positions in gap 24 close to anodes 18, as described hereinabove for detector 10. Alternatively, light source 62 is scanned by other methods known in the art. Most preferably, the scanning of mirror 64 is controlled by unit 17, wherein signals from detectors 60 are processed as described hereinabove.

It will be appreciated that other detecting systems having detectors with combined anode and/or cathode arrays and optical irradiators may also be used advantageously in other contaminant detecting systems. All such arrangements, and their use in detecting contaminants, are considered to be within the scope of the present invention. The principles of the present invention thus enable detecting systems to detect contaminants with higher efficiency and reduced false negative results, compared to detecting systems at present known in the art.

It will be further appreciated that the preferred embodiments described above are cited by way of example, and the full scope of the invention is limited only by the claims.

What is claimed is:

1. Apparatus for detecting a contaminant in a substrate, comprising:

an irradiator which irradiates the substrate with photons having energies below an atomic ionization energy of the substrate, so as to ionize the contaminant to produce electrons;

an array of anode elements, which is positioned adjacent to the substrate and biased at a positive voltage with respect thereto, so as to collect the electrons, thereby generating a current indicative of the presence of the contaminant in the substrate; and a scanner, which scans the array over a surface of the substrate.

2. Apparatus for detecting a contaminant in a substrate, comprising:

an irradiator which irradiates the substrate with photons having energies below an atomic ionization energy of the substrate, so as to ionize the contaminant to produce electrons;

an array of anode elements, which is positioned adjacent to the substrate and biased at a positive voltage with respect thereto, so as to collect the electrons, thereby generating a current indicative of the presence of the contaminant in the substrate; and an array of cathode elements positioned in proximity to the substrate and to the array of anodes and biased at a negative voltage relative to the substrate.

3. Apparatus according to claim 2, wherein the cathode elements are biased so as to enhance the current indicative of the presence of the contaminant.

4. Apparatus according to claim 2, wherein the cathode elements are biased so as to discriminate between currents created by different types of contaminant.

5. Photoionization detector apparatus, comprising:

a transparent plate, which is brought into proximity with a material to be photoionized and through which a beam of radiation impinges on the material; and a first and a second linear array of electrodes separated by a linear aperture, which electrodes are formed on a surface of the plate adjacent to the material and are electrically biased relative to the material, so as to collect charged particles emitted from the material responsive to the beam of radiation.

6. Apparatus according to claim 5, wherein the first linear array comprises an anode array, and the second linear array comprises a cathode array.

7. Photoionization detector apparatus, comprising:

a transparent plate, which is brought into proximity with a material to be photoionized and through which a beam of radiation impinges on the material;

an array of electrodes, formed on a surface of the plate adjacent to the material and electrically biased relative to the material, so as to collect charged particles emitted from the material responsive to the beam of radiation; and a positioning device for maintaining a constant distance between the material and the array, wherein the positioning device comprises an array scanner, which scans the array over the material.

8. Photoionization detector apparatus, comprising:

a transparent plate, which is brought into proximity with a material to be photoionized and through which a beam of radiation impinges on the material;

an array of electrodes, formed on a surface of the plate adjacent to the material and electrically biased relative to the material, so as to collect charged particles emitted from the material responsive to the beam of radiation; and a beam scanner which scans the beam of radiation over the material.

* * * * *